United States Patent [19]

Pohndorf

[11] Patent Number: 5,036,862
[45] Date of Patent: Aug. 6, 1991

[54] IMPLANTABLE, SELF-RETAINING LEAD

[75] Inventor: Peter J. Pohndorf, Raleigh, N.C.

[73] Assignee: Cordis Corporation, Miami Lakes, Fla.

[21] Appl. No.: 34,697

[22] Filed: Apr. 6, 1987

[51] Int. Cl.⁵ .............................................. A61N 1/02
[52] U.S. Cl. ................................................... 128/784
[58] Field of Search .................... 128/783–786, 128/419 P, 419 PS; 439/11, 13, 784–785

[56] References Cited

U.S. PATENT DOCUMENTS

| | | | |
|---|---|---|---|
| Re. 31,990 | 9/1985 | Slvetz et al. ........... | 128/784 X |
| 3,757,789 | 9/1973 | Shanker .................. | 128/786 |
| 4,387,727 | 6/1983 | Sandstrom .............. | 128/784 |
| 4,411,276 | 10/1983 | Dickhudt et al. ....... | 128/784 |
| 4,411,277 | 10/1983 | Dickhudt ................ | 128/784 |
| 4,516,584 | 5/1985 | Garcia .................... | 128/785 |
| 4,553,961 | 11/1985 | Pohndorf et al. ....... | 128/784 X |
| 4,624,266 | 11/1986 | Kane ...................... | 128/785 |
| 4,628,973 | 12/1986 | Miller .................... | 128/785 |
| 4,667,686 | 5/1987 | Peers-Trevarton ..... | 128/785 |
| 4,672,979 | 6/1987 | Pohndorf ................ | 128/784 |
| 4,683,895 | 8/1987 | Pohndorf ................ | 128/784 |

Primary Examiner—William E. Kamm
Attorney, Agent, or Firm—Gerstman & Ellis, Ltd.

[57] ABSTRACT

An electrical lead for implantation in a patient comprises separate first and second lead portions having conductor wire therein. The leads are electrically connected at respective ends within a lead anchor member. In accordance with this invention, the lead anchor has means for fixed retention of the first and second lead portions in electrical connection therewith so that an electrical signal passing through the lead passes through a conductive portion of the lead anchor between the first and second lead portions. The lead anchor has means permitting suture retention in a desired implanted position in the patient.

4 Claims, 1 Drawing Sheet

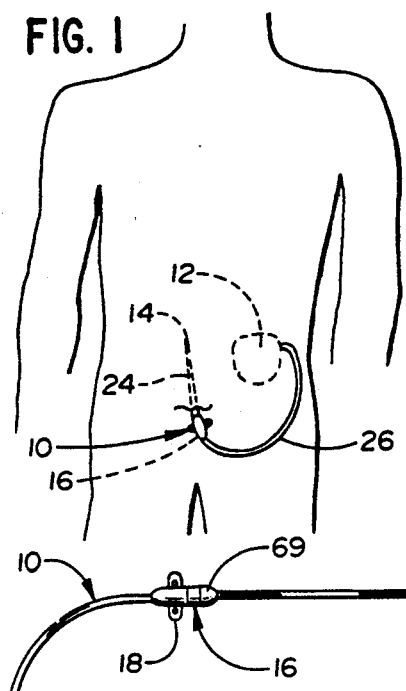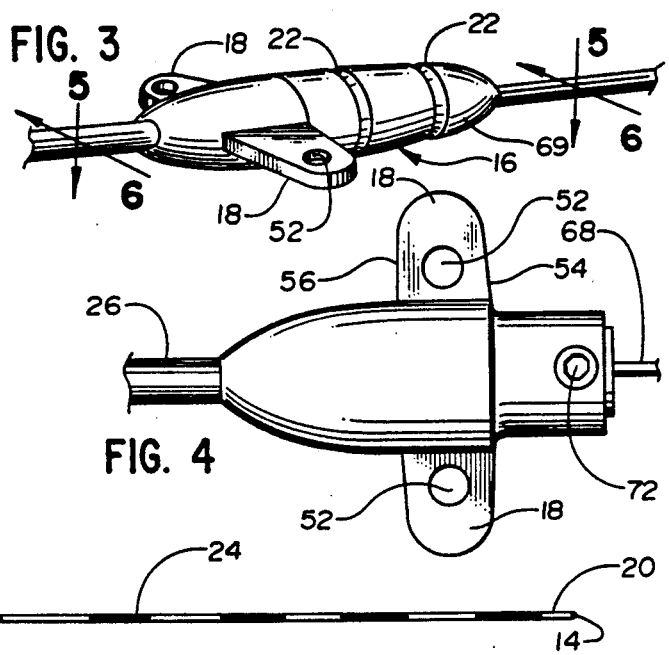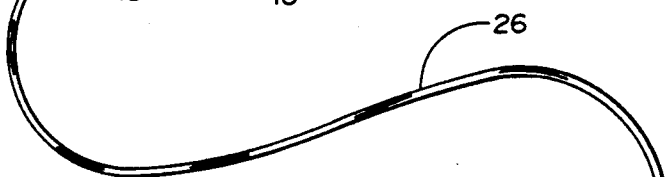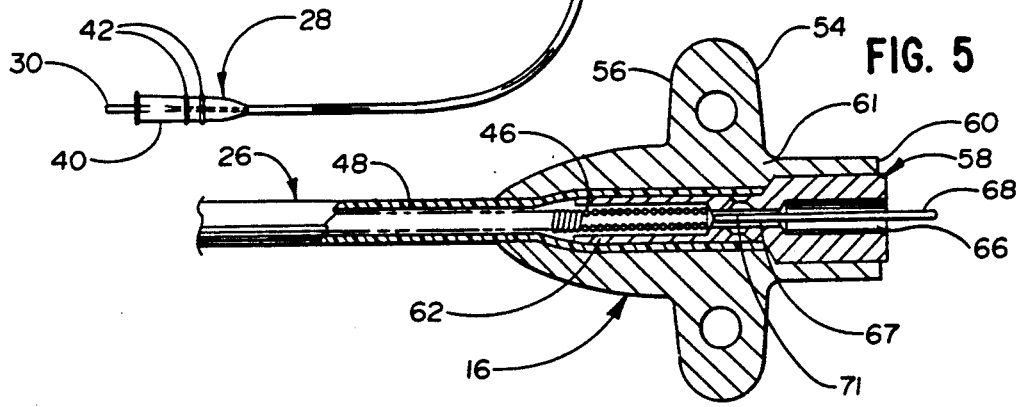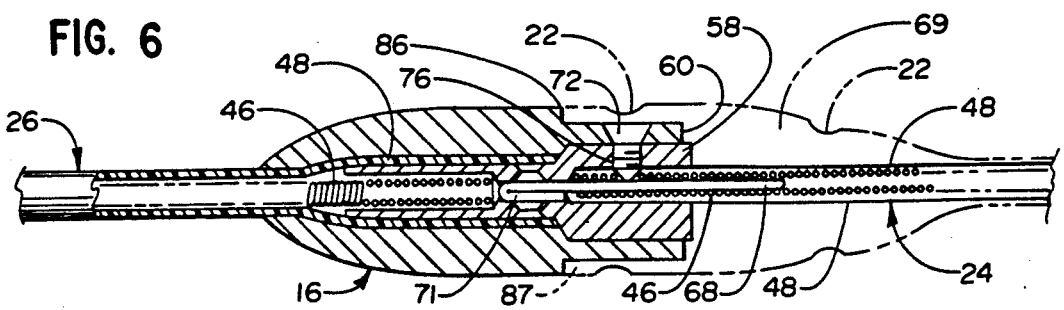

IMPLANTABLE, SELF-RETAINING LEAD

BACKGROUND OF THE INVENTION

This application relates to electrical leads which are intended for implantation in the patient for numerous uses such as cardiac pacing or sensing, or any other desired use. Particularly, the lead of this invention is contemplated for use as part of a spinal lead system, in which, as is conventionally known, electrical current is applied to the spinal cord as a method of alleviating lower back pain. Such a lead is used to place an electrode in the epidural space of the spine. The lead may be adjusted in its position with current applied on an experimental basis until the patient reports the best paresthesia in a given position. At that point, or at a later time, the surgeon may implant, subcutaneously, a neurostimulator, and connect it to the positioned lead for transferring neurostimulating signals to the spinal cord.

In the prior art, a separate lead anchor is generally affixed in the area of the spinal lead's exit from the spinal column, and sutured to the patient. The purpose of this is, of course, to maintain the optimum position of the lead in the spinal column for maximum pain suppressing effect. The anchor may typically be sutured to the underlying muscle, with sutures also tied around the body of the anchor, while the lead itself is positioned within the anchor in telescoping relation thereto for retention.

Unfortunately, it has been found that, as the patient moves, it is possible for the lead to slide to a certain extent with respect to the lead anchor. This, in turn, results in a shifting of the position of the electrode in the epidural space, which may reduce the effectiveness of the pain-reducing electrical stimulation through the electrode. However, this problem has not been easily solved, because the precise positioning of the lead anchor on the lead cannot be exactly determined until actual implantation has taken place and after the electrode on the lead has been precisely positioned. Accordingly, the lead anchor cannot be preattached to the lead in a manner to effect permanent, non-sliding attachment, because of the unpredictability of the positioning of the lead tip and its electrode in the spine, coupled with the requirement for the lead anchor to be positioned at only about one possible position, at the spinal lead's exit from the patient.

For this reason, in the prior art, a lead anchor with a sliding connection with the lead that it retains has been mandatory.

In accordance with this invention, an improved electrical lead is provided, in which an attached lead anchor means may be adjustably positioned with respect to the lead. Nevertheless, the lead anchor cannot slide along the lead, so that an electrical lead may be provided for implantation with adjustable lead anchor positioning, but without the problem of the prior art of migration of the lead within the spine after the implantation procedure is complete. It can be understood that such migration is very unpleasant because it may require another operation to readjust the positioning of the lead, which of course is very traumatic to the patient and highly undesirable.

DESCRIPTION OF THE INVENTION

In this invention an electrical lead is provided for implantation in a patient. The lead comprises separate, first and second lead portions having conductor wire therein which is typically enclosed with insulation in conventional manner. The first and second lead portions are electrically connected at respective ends within lead anchor means.

In accordance with this invention, the lead anchor means have means for fixed retention of the first and second lead portions in electrical connection therewith so that an electrical signal passing through the lead passes through a conductive portion of the lead anchor means between the first and second lead portions. The lead anchor means has means permitting suture retention in a desired implanted position in the patient.

Thus, by this invention, the first lead portion, when used as a spinal lead, may be adjusted in the spine in conventional manner until the maximum paresthesia is reported by the patient. Then, the lead anchor means may be connected to the outer end of the first lead. Typical+y, the lead anchor means will have already been connected to the distal end of the second lead, so that the two leads enter into electrical connection with each other through the lead anchor means. Then, the lead anchor means may be sutured into position, and the second lead portion attached to the neurostimulator, which is typically implanted subcutaneously, so that the entire system may be enclosed within the skin. In this invention, particularly the connection of the lead anchor means and the first lead portion is of a non-sliding nature so that movements by the patient in his daily activities are much less likely to push the free, distal end of the first lead portion out of the desired position.

Typically, the fixed retention means of the lead anchor includes a conductive metal sleeve positioned within the lead anchor, the sleeve having a bore portion which carries a conductive metal pin in electrically conductive relation to the sleeve, said pin being positioned in said bore portion and in electrically conductive, engaging relation with the conductor wire of one of said lead portions, typically the first lead portion. Thus, electrical connection is provided between the conductive metal sleeve and the lead portion.

One end of the sleeve may define a tubular portion surrounding a portion of the conductor wire of the other of said lead portions in electrical connection therewith.

Also, the conductive metal sleeve may define a lateral, threaded aperture which carries a threaded pressure member for pressing the conductor wire of the one lead portion into firm engagement with the pin, for good electrical connection and firm retention. This pressure member may be a simple screw or bolt movable in a threaded seat of the sleeve, which may be screwed into place during installation of the connection between the lead anchor means and the engaging lead portion during the connection thereof.

After adjustment of the first lead portion to the desired position, it may be cut to desired length immediately prior to connection with the lead anchor means. Thus, an adjustable lead system is provided in which both the electrode-carrying tip of the first lead portion and the lead anchor means may be properly positioned in adjusted relation, but slippage of the lead anchor means along the lead after implantation cannot take place, so that surgical readjustment of the lead system is needed with much less frequency.

DESCRIPTION OF THE DRAWINGS

In the drawings, FIG. 1 is a diagrammatic view showing a spinal lead system of this invention implanted in a patient;

FIG. 2 is a plan view of a spinal lead in accordance with this invention

FIG. 3 is a fragmentary enlarged perspective view of the spinal lead of FIG. 2;

FIG. 4 is a plan view of the spinal lead of FIG. 3, with the first lead portion removed;

FIG. 5 is a sectional view taken along line 5—5 of FIG. 3 with one lead unattached; and FIG. 6 is a sectional view taken along line 6—6 of FIG. 3.

DESCRIPTION OF SPECIFIC EMBODIMENTS

Referring to the drawings, electrical lead system 10 is disclosed. Electrical lead system 10 is shown in FIG. 1 to be implanted within the patient and coupled at one end to neural stimulator 12, of conventional design, while the other end 14 of lead system 10 carries an electrode 20 (FIG. 2) for nerve stimulation. Lead anchor 16 is provided at a point between the ends of lead 10 and is adapted for permitting suture retention thereof in a desired implanted position in the patient. As shown, lead anchor 16 may carry perforated wings 18 for suturing, and a boot or cover 69 having circumferential grooves 22 for further suture retention.

Electrical lead 10 includes first lead portion 24 and second lead portion 26, each of which are separate from each other and which are attached at one end as shown to lead anchor 16 in electrical connection therewith so that an electrical signal passing through either lead passes through a conductive portion of lead anchor 16 and then the other lead.

Second lead portion 26 is terminated at its proximal end with electrical connector or terminal means 28 of conventional design for electrical connection with neural stimulator 12. Terminal means 28 includes a conductive terminal pin 30, a portion of the length of which is sheathed in a silicone elastomer sleeve 40, having projecting annular ridges 42 to prevent fluid intrusion into the coupling area of terminal 28 and neural stimulator 12.

Electrode 20 may be conventionally made of platinumiridium, and exposed for placement against the epidural surface of the spinal cord. Each of lead portions 24, 26 may comprise lengths of coiled conductor wire 46 enclosed in a polyurethane sheath. Pin 30 is permanently connected in electrically conductive relation to the coiled conductor 46 of second lead portion 26.

Lead anchor 16 receives and retains the respective ends of first and second lead portions 24, 26 as specifically shown in FIGS. 5 and 6. If desired, the leading edge 54 of each laterally projecting wing 18 may be longer than the trailing edge 56 thereof. Apertures 52 are provided in each wing 18 as suture holes.

Inside of lead anchor 16, conductive metal collet 58, made for example of stainless steel, is provided, with collet 58 extending slightly beyond distal end 60 of the outer casing 61 of lead anchor 16. Collet 58 also defines projecting tubular flange portion 62, into which the coiled conductive wire 46 of lead portion 26 extends, being bonded therein by welding, soldering, or crimping to flange portion 62 to provide electrical connection between collet 58 and lead portion 26. Insulating sheath 48 of second lead portion 26 may also extend into the outer casing 61 of coupling terminal 16, and may surround the outer surface of flange 62. Thus, second lead portion 26 is firmly and permanently attached to collet 58.

Collet 58 also defines a relatively enlarged central lumen 66 at one outer end thereof, and a reduced sized portion 67 centrally located within lead anchor 16. Core pin 68 is bonded to collet 58 and positioned within lumen 66, being retained frictionally or soldered into retentive relation with the bore of reduced diameter portion 67. A double folded portion 71 of pin 68 may be used, so that pin 68 is in firmly retained electrical connection with collet 58.

As shown in FIG. 6, set screw 72 resides in a threaded aperture 76 of collet 58. After first lead section 24 has been properly positioned, its end may be cut and inserted into lead anchor 16 t the position shown. The spiral wire conductor array 46 of first lead portion 24 may be penetrated by pin 68 as shown. Set screw 72 is than advanced to firmly press conductor wires 46 into electrically conductive relation with pin 68 and collet 58, while at the same time providing firm retention of first lead portion 24 so that it cannot be pulled out of its position. Screw 72 may have a pointed front end to penetrate the insulating sheath 48 of first lead portion 24 for added electrical connection possibilities between conductive wires 46 and collet 58 through set screw 72.

After the above described connections have been made between lead anchor 16 and first and second lead portions 24, 26, silicone rubber tubular boot 69, threaded upon first lead portion in sliding relation therewith, may be drawn up into engaging relation with lead anchor 16 as shown in FIGS. 3 and 6, for example. Boot 69 may have annular suturing grooves 22 defined therein as shown, and may be glued into place with an appropriate, physiologically acceptable adhesive such as RTV silicone adhesive.

After connection has been made between lead anchor 16 and the two lead portions 24, 26, lead anchor 16 may be sutured into its desired position adjacent the exit site of first lead portion 24 from the spinal area. The remaining portion of the lead system, second lead 26,may have been installed in a previously made tunnel in the patient to communicate between lead anchor 16 adjacent the spinal column and the site of permanent implatation of neural stimulator 12.

By this means, a reliable electrical connection is provided between stimulator 12 and electrode 20, with electrical signals passing through second lead portion 26, collet 58, and first lead portion 24.

It can be seen that step 86 is provided in the body of lead anchor 16 so that thin annular flange 87 of boot 69 may form a relatively smooth transition between the two parts, as shown in FIG. 6. Thus, an electrical lead for implantation is shown in which a lead anchor may be precisely positioned along the lead, but the risk found in the prior art of slippage of such lead anchor has been eliminated.

The above is offered for illustrative purposes only, and is not intended to limit the scope of the invention of this application, which is defined in the claims below.

That which is claimed is:

1. In an electrical lead for implantation in a patient which comprises separate first and second lead portions having conductor wire therein, electrically connected at respective ends within lead anchor means, the improvement comprising, said lead anchor means including a conductive metal sleeve, said sleeve including means for fixed retention of said first and second lead portions in electrical connection therewith, said sleeve having a bore portion which carries a conductive metal pin in electrically conductive relation to said sleeve, said pin being positioned in electrically conductive, engaging relation with the conductor wire of one of said lead portions, said sleeve also defining a lateral, threaded aperture which carries a threaded pressure member for pressing the conductor wire of said one lead portion into firm engagement with said pin for good electrical connection and firm retention.

2. The electrical lead of claim 1 in which one end of said sleeve, spaced from said lateral, threaded aperture, defines a tubular portion surrounding and retaining a portion of the conductor wire of the other of said lead portions in electrical connection therewith.

3. The lead of claim 2 in which said first lead portion carries an external electrode at its end opposed to said lead anchor means, and said second lead portion carries electrical connector means at its end opposed to said lead anchor means.

4. The electrical lead of claim 3 in which said lead anchor means has means permitting suture retention in a desired, implanted position in the patient.

* * * * *